US006432119B1

(12) United States Patent
Saadat

(10) Patent No.: US 6,432,119 B1
(45) Date of Patent: *Aug. 13, 2002

(54) APPARATUS AND METHODS FOR PERFORMING PERCUTANEOUS MYOCARDIAL REVASCULARIZATION AND STIMULATING ANGIOGENESIS USING AUTOLOGOUS MATERIALS

(75) Inventor: Vahid Saadat, Redwood Shores, CA (US)

(73) Assignee: Angiotrax, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/428,698

(22) Filed: Oct. 27, 1999

Related U.S. Application Data

(63) Continuation-in-part of application No. 09/274,790, filed on Mar. 23, 1999, now Pat. No. 6,102,926, and a continuation-in-part of application No. 09/271,094, filed on Mar. 17, 1999, now Pat. No. 6,120,520.

(51) Int. Cl.$^7$ ............................................... A61B 17/32

(52) U.S. Cl. ..................................... 606/170; 600/564

(58) Field of Search ............................... 606/1, 14, 45, 606/46, 108, 159, 170, 171, 180, 564, 565; 128/898

(56) References Cited

U.S. PATENT DOCUMENTS

| 4,479,896 A | 10/1984 | Antoniades |
| 4,957,742 A | 9/1990 | Knighton |
| 5,834,418 A | 11/1998 | Brazeau et al. |
| 5,840,059 A | 11/1998 | March et al. |
| 5,846,225 A | 12/1998 | Rosengart et al. |
| 5,899,874 A | 5/1999 | Jonsson |
| 5,906,594 A | 5/1999 | Scarfone et al. |

FOREIGN PATENT DOCUMENTS

| EP | 0 853 921 A2 | 7/1998 |
| WO | WO 86/03122 | 6/1986 |
| WO | WO 96/35469 | 11/1996 |
| WO | WO 98/05307 | 2/1998 |
| WO | WO 98/17186 | 4/1998 |

OTHER PUBLICATIONS

Fenton II, John W. et al., "Thrombin and Antithrombotics," Seminars in Thrombosis and Hemostasis, vol. 24, No. 2, 1998, pp. 87–91.

Folkman, Judah, "Angiogenic Therapy of the Human Heart," Circulation, 1998; 97:628–629.

Henry, Timothy D., "Can We really Grow New Blood Vessels," The Lancet, vol. 351, Jun. 20, 1998, pp. 1826–1827.

Knighton, David R. et al., "Role of Platelets and Fibrin in the Healing Sequence," Annals of Surgery, vol. 196, No. 4, Oct. 1982, pp. 379–388.

Losordo, Douglas W. et al., "Gene Therapy for Myocardial Angiogenesis Initial Clinical Results With Direct Myocardial Injection of phVEGF$_{165}$ as Sole Therapy for Myocardial Ischemia," Circulation, 1998; 98:2800–2804.

Maloney, James P. et al., "In Vitro Release of Vascular Endothelial Growth Factor During Platelet Aggregation," American Physiological Society, H1054–H1061, 1998.

(List continued on next page.)

Primary Examiner—Kevin T. Truong
(74) Attorney, Agent, or Firm—Fish & Neave; Nicola A. Pisano

(57) ABSTRACT

Methods are provided for collecting and processing autologous biological materials to form autologous angiogenic agents. Apparatus and methods also are provided for performing percutaneous myocardial revascularization wherein an injection needle is disposed in spaced-apart relation to the channel-forming tool, so that a predetermined amount of the autologous angiogenic agent may be injected into the myocardium adjacent to the PMR channel.

34 Claims, 4 Drawing Sheets

OTHER PUBLICATIONS

Miyazono, Kohei et al., "Platelet–Derived Endothelial Cell Growth Factor," *Progress in Growth Factor Research*, vol. 3, 1991, pp. 207–217.

Pipili–Synetos, E. et al., "Evidence That Platelets Promote Tube Formation By Endothelial Cells on Matrigel," *British Journal of Pharmacology*, vol. 125, 1998, pp. 1252–1257.

Simons, Michael et al., "Food for Starving Hearts," *Nature Medicine*, vol. 2, No. 5, May 1996, pp. 519–520.

Tsopanoglou, Nikos E. et al., "Thrombin Promotes Angiogenesis By a Mechanism Independent of Fibrin Formation," *American Physiological Society*, 0363–6143/93, C1302–1307.

Verheul, Henk M.W. et al., "Platelet: Transporter of Vascular Endothelial Growth Factor," *Clinical Cancer Research*, vol. 3, Dec. 1997, pp. 2187–2190.

Wartiovaara, Ulla et al., "Peripheral Blood Platelets Express VEGF–C and VEGF Which Are Released During Platelet Activation," *Thromb Haemost*, 1998, 80:171–5.

A Collection of Abstracts, *Society of Thoracic Surgeons*, 1999.

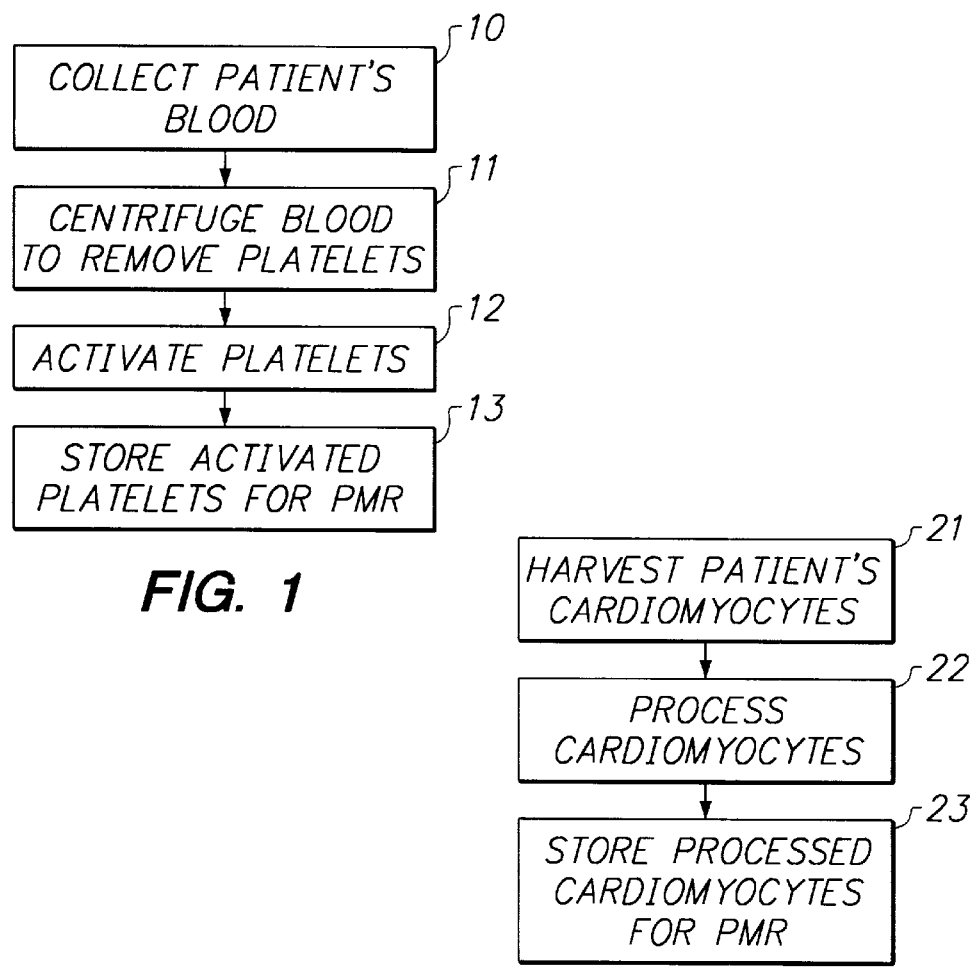
FIG. 1
FIG. 2
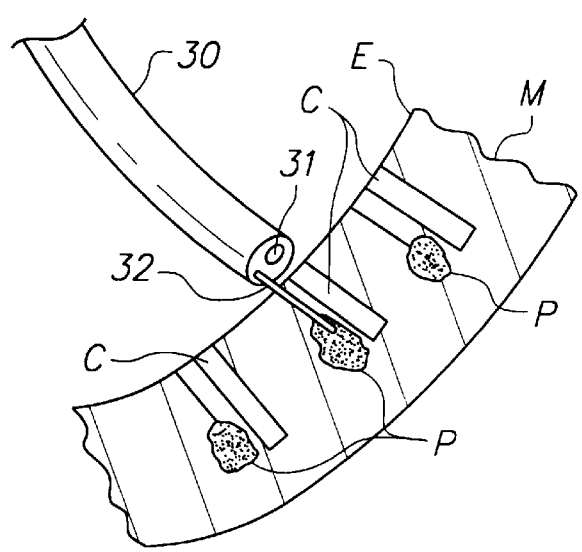
FIG. 3

APPARATUS AND METHODS FOR PERFORMING PERCUTANEOUS MYOCARDIAL REVASCULARIZATION AND STIMULATING ANGIOGENESIS USING AUTOLOGOUS MATERIALS

REFERENCE TO RELATED APPLICATIONS

The present application is a continuation-in-part of U.S. patent application Ser. No. 271,094 filed Mar. 17, 1999 now U.S. Pat. No. 6,120,520 and U.S. patent application Ser. No. 09/274,790, filed Mar. 23, 1999 now U.S. Pat. No. 6,102,926.

FIELD OF THE INVENTION

The present invention relates to apparatus and methods for performing percutaneous myocardial revascularization and injecting autologous materials into the treated tissue to stimulate angiogenesis.

BACKGROUND OF THE INVENTION

A leading cause of death in the United States today is coronary artery disease, in which atherosclerotic plaque causes blockages in the coronary arteries, resulting in ischemia of the heart (i.e., inadequate blood flow to the myocardium). The disease manifests itself as chest pain or angina. In 1996, approximately 7 million people suffered from angina in the United States.

One technique that has been developed to treat patients suffering from diffuse atherosclerosis, is referred to as percutaneous myocardial revascularization (PMR). In this method, a series of channels are formed in the left ventricular wall of the heart extending inward from the myocardium. Typically, between 15 and 30 channels about 1 mm in diameter and preferably several millimeters deep are formed with a laser in the wall of the left ventricle to perfuse the heart muscle with blood coming directly from the inside of the left ventricle, rather than traveling through the coronary arteries. Commonly assigned U.S. Pat. No. 5,910,150 to Saadat describes mechanical apparatus for forming such channels. PCT Publication WO 98/17186 describes a laser-based system for performing PMR that includes needle adjacent to the laser element for injecting a contrast agent to mark the position of the PMR channels for imaging.

U.S. Pat. No. 5,840,059 to Mar. et al. describes a laser-based PMR system that deposits a angiogenic agent, such as a gene vector or genetically engineered harvested cells, into the channel formed during the PMR procedure to promote angiogenesis. A drawback of this approach, however, is that blood pulsing through the PMR channel during normal cardiac wall motion may cause the angiogenic factor to be promptly washed out of the channel, thereby dissipating any beneficial effect obtainable from its introduction.

In addition, it is relatively difficult and expensive to use engineer and produce the kinds of angiogenic factors referred to in the foregoing patent.

Accordingly, it would be desirable to provide apparatus and methods for delivering angiogenic agents in conjunction with PMR treatments that promote long-term residence of the angiogenic agent in the vicinity of the treated tissue. It further would be desirable to provide relatively low-cost and readily available or readily prepared angiogenic agents for use in conjunction with PMR.

Wartiovaara et al., "Peripheral Blood Platelets Express VEGF-C and VEGF which Are Released During Platelet Activation," *Thromb Haemost*, 80:171–175 (1998), describes that a variety of vascular endothelial growth factors (VEGF) may be derived from platelets. Knighton et al., "Role of Platelets and Fibrin in the Healing Sequence, "*Ann. Surg.*, 196(4)379–388 (1982), which is incorporated herein by reference, describes that thrombin-activated platelets, when injected in vivo in rabbit corneas, produced neovascularization that was dose related. U.S. Pat. Nos. 4,957,742 to Knighton, U.S. Pat. No. 4,479,896 to Antoniades, and U.S. Pat. No. 5,834,418 to Brazeau describe methods of extracting platelet growth factors from blood.

Sakai et al., "Autologous Cardiomyocyte Transplantation Improves Cardiac Function After Myocardial Injury," presented at the 1999 STS Convention, San Antonio, N. Mex., Jan. 1999, suggests that autologous cardiomyocytes may be harvested, cultured and re-injected into injured myocardium to restore ventricular function.

In view of the foregoing, it would be desirable to provide apparatus and methods for using autologous materials in conjunction with PMR to augment angiogenesis resulting from forming myocardial channels.

It further would be desirable to provide apparatus and methods that reduce the risk of such autologous angiogenic materials from washing out of the PMR channels, and instead promote retention of such materials by injecting the angiogenic materials into the myocardium adjacent to the PMR channels.

SUMMARY OF THE INVENTION

In view of the foregoing, it is an object of this invention to provide apparatus and methods for delivering angiogenic agents in conjunction with PMR treatments that promote long-term residence of the angiogenic agent in the vicinity of the treated tissue.

It is another object of the present invention to provide apparatus and methods for conveniently and economically preparing autologous angiogenic agents for use in conjunction with PMR.

It is another object of this invention to provide apparatus and methods for using autologous materials in conjunction with PMR to augment angiogenesis resulting from forming myocardial channels.

It is also an object of the present invention to provide apparatus and methods that reduce the risk of such autologous angiogenic materials from washing out of the PMR channels, and instead promote retention of such materials.

It is a further object of the present invention to provide apparatus and methods for performing percutaneous myocardial revascularization that enable autologous angiogenic agents, such as platelets, platelet derived growth factors or cardiomyocytes to be injected into the myocardium adjacent to the PMR channels.

These and other objects of the present invention are accomplished by providing methods for collecting and processing autologous biological materials to form autologous angiogenic agents.

Apparatus and methods also are provided for performing percutaneous myocardial revascularization that includes an injection needle disposed in spaced-apart relation to the channel-forming tool, so that a predetermined amount of the autologous angiogenic agent may be injected into the myocardium adjacent to the PMR channel.

In accordance with the principles of the present invention, blood, cardiomyocytes, or other biological material is first collected from a patient scheduled to undergo PMR. The biological material is then treated to concentrate and activate or express one or more platelet derived growth factors, and is stored in preparation for re-injection into the patient's myocardium during a PMR procedure.

Apparatus suitable for implementing the methods of the present invention comprises a catheter having an end region that is directable to contact a patient's endocardium at a plurality of positions. Preferably, the catheter comprises inner and outer catheters each having preformed distal bends, so that the distal end of the inner catheter is directable to a plurality of positions. A cutting head is disposed within a lumen of the inner catheter and coupled to a drive tube that rotates and reciprocates the drive shaft. The drive tube is coupled to a motor that imparts rotational motion to the drive tube. The cutting head and drive tube include a lumen through which severed tissue is aspirated.

One or more stabilizing elements, are disposed on the distal end to retain the inner catheter in position while the cutting head is reciprocated beyond a distal endface of the inner catheter. In accordance with the present invention, the stabilizing elements also serve as injection needles for the re-injecting autologous angiogenic agent into the patient's myocardium in the vicinity of the channels formed by the cutting head. Methods of using the apparatus to deliver angiogenic agents also are described.

BRIEF DESCRIPTION OF THE DRAWINGS

Further features of the invention, its nature and various advantages will be more apparent from the accompanying drawings and the following detailed description of the preferred embodiments, in which:

FIG. 1 is a flow chart illustrating steps of collecting and processing blood to prepare autologous angiogenic agents;

FIG. 2 is a flow chart for an alternative method of the present invention wherein cardiomyocytes are collected and processed for re-injection into a patient's myocardium;

FIG. 3 is an illustrative view of a distal end of apparatus of the present invention injecting boluses of autologous angiogenic material adjacent to channels formed by the device;

DETAILED DESCRIPTION OF THE INVENTION

Figure 4:
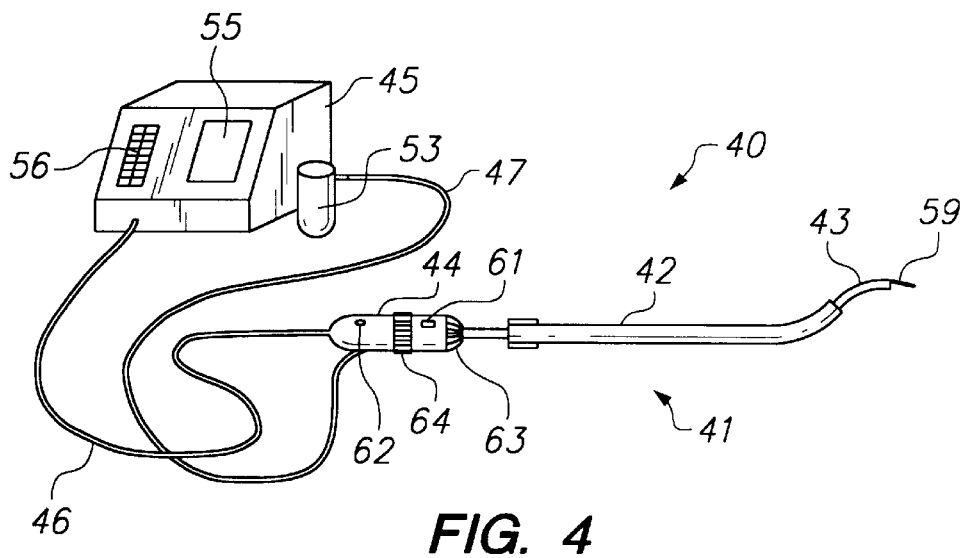
FIG. 4 is a perspective view of an illustrative embodiment of apparatus suitable for implementing the methods of the present invention.

The present invention provides methods for collecting and preparing autologous biological materials to form angiogenic agents, and apparatus for injecting those angiogenic agents into a patient's myocardium in the vicinity of chan-nels formed by PMR. In accordance with the methods of the present invention, a series of channels is cut into the myocardium using a rotating cutting head through which severed material is aspirated. A stabilizer element fixed in a spaced-apart relation to the cutting head is employed to inject the autologous angiogenic material into pockets in the vicinity of the PMR channel. Advantageously, the angiogenic material disposed within pockets may migrate to towards the PMR channels to enhance revascularization, without being washed out of the PMR channel as in previously known methods.

Referring to FIG. 1, a first illustrative method of providing autologous angiogenic agents is described. A patient scheduled for a PMR procedure arranges to visit the hospital or clinic where the procedure is to be performed several days in advance of the procedure, and a quantity of whole blood is collected at step 10.

At step 11, the blood is then centrifuged using any of a number of previously known techniques, e.g., such as described in the foregoing patent to Knighton, to obtain a platelet rich plasma. The resulting platelet-rich plasma may be further centrifuged, and the platelet concentrate resuspended in a buffered solution to a concentration of about a million platelets per milliliter or less.

At step 12, the platelets are activated using one of a number of known techniques, and preferably by being exposed to thrombin about 1 to 10 units of purified thrombin per ml of resuspended platelet material, again as described in the above-incorporated article by Knighton. At step 13, the resulting angiogenic agent is filled in appropriately sized vials for use in conjunction with the patient's PMR procedure and stored under refrigeration, until the day of the PMR procedure.

Other methods for preparing an angiogenic agent from the patient's blood also may be employed, as described in the above-referenced articles. It is sufficient for the method illustrated in FIG. 1 that, at the end of the collection and processing step, an angiogenic platelet-rich agent has been prepared, at a much lower cost than associated with the production of gene vectors such as described in the aforementioned Mar. et al. patent.

Referring to FIG. 2, an alternative method of collecting and preparing an autologous angiogenic agent is described. In this method, prior to the date of a scheduled PMR procedure, the patient arranges to visit the hospital or clinic to have a number of cells harvested. For example, using the PMR device described in the aforementioned patent to Saadat, which is incorporated herein by reference, a quantity of myocardial cells may be harvested, at step 21. Alternatively, other suitable cells, such as bone marrow cells, may be extracted.

At step 22, the harvested cells are processed and prepared for use in conjunction with the subsequent PMR procedure. For example, the harvested cells may be cultured, using techniques which are per se known and described in the above-mentioned work of Sakai. At step 23, the harvested cells are then divided and suspended in an appropriately buffered solution. The resulting angiogenic agent is filled in appropriately sized vials and stored awaiting re-injection during the PMR procedure.

Referring now to FIG. 3, illustrative methods of injecting an autologous angiogenic agent in conjunction with PMR are described. In FIG. 3, distal end 30 of PMR apparatus, as described hereinbelow, is disposed adjacent to endocardium E in a patient's left ventricle. Reciprocable cutting head 31 of the PMR apparatus is used to bore channels C into myocardium M through the endocardial surface.

In accordance with the methods of the present invention, hollow reciprocable stabilizer needle 32 is used to inject a bolus of a predetermined quantity of autologous angiogenic agent into "pocket" P adjacent to channel C upon completion of the channel-forming operation of cutting head 31. Advantageously, the angiogenic agent is expected to migrate from the pocket P towards the channel over a period of time, thereby enhancing revascularization, but without having the angiogenic agent washed out of the channel during normal wall motion.

Figure 5:
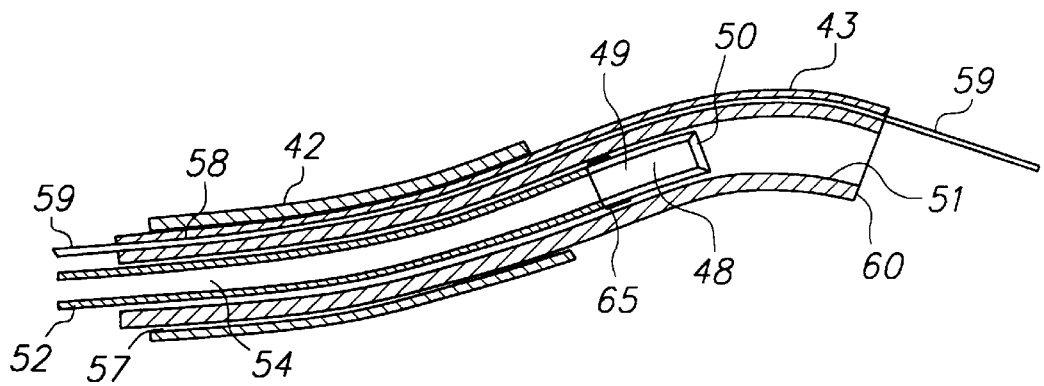
FIG. 5 is a partial sectional view of the distal region of the apparatus of FIG. 1.

Referring now to FIGS. 4 and 5, illustrative apparatus 40 suitable for practicing the methods of the present invention is described. Apparatus 40 includes device 41 comprising handle 44 having inner catheter 43 disposed within outer guide catheter 42, and coupled to controller 45 via cable 46 and vacuum hose 47. Cutting head 48 having lumen 49 and sharpened distal end 50 is disposed within lumen 51 of inner catheter 43. Cutting head 48 is coupled to drive tube 52, which in turn is coupled via cable 46 to a drive system contained in controller 45 that imparts rotational and longitudinal motion to drive tube 52 and cutting head 48. Suction is drawn through lumen 49 of cutting head 48 and drive tube 52 to aspirate tissue severed by the cutting head to tissue trap 53 connected to controller 45 via vacuum hose 47.

Controller 45 comprises a vacuum pump or vacuum canister (not shown) that draws suction through lumen 54 of drive tube 52 via hose 47, a drive train (not shown) including a motor and gearing that impart rotational motion to drive tube 52 via cable 46, and a linear actuator mechanism (e.g., electromechanical or pneumatic) that reciprocates drive tube 52 and cutting head 48 within lumen 51 of inner catheter 43. Controller 45 also includes display panel 55, input panel 56 (e.g., a plurality of selector switches) and circuitry (see FIG. 7) for controlling operation of device 41. Further details of controller 45 are described in the above-incorporated patent to Saadat.

Inner catheter 43 is disposed for movement, either rotational, longitudinal or both, within lumen 57 of outer guide catheter 42. Inner catheter 43 further includes lumen 58 through which hollow needle stabilizer 59 may be reciprocated from a retracted position, within lumen 58, to an extended position, extending beyond distal endface 60 of inner catheter 43 (as shown in FIG. 5). A proximal end of hollow needle stabilizer 59 is coupled to slider button 61 of handle 44. When moved to the extended position, needle stabilizer 59 retains the distal end of inner catheter 43 in position with respect to an endocardial surface, and counteracts reaction forces generated when cutting head 48 is actuated.

Figure 6:
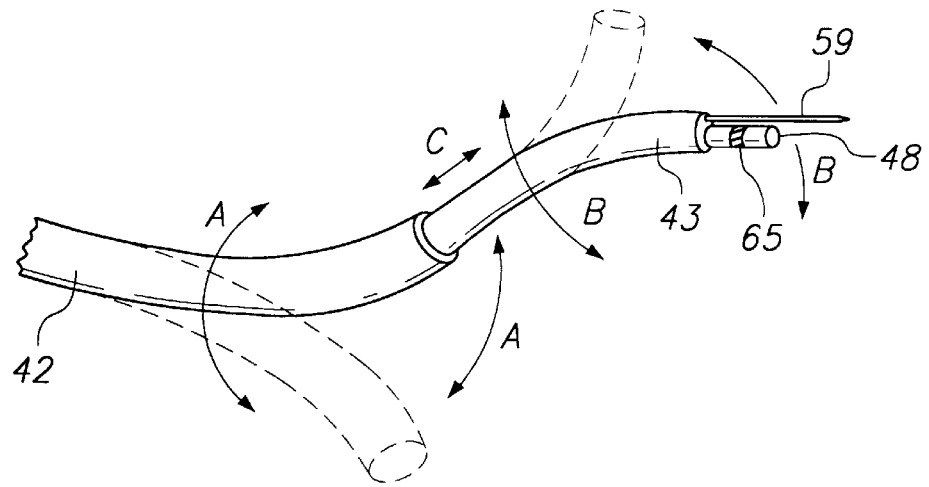
FIG. 6 is a perspective view illustrating how the inner and outer catheters can be rotated to position the distal end of the inner catheter at a plurality of positions.

Cutting head 48 and drive tube 52 are coupled via cable 46 to a drive train that moves cutting head 48 from a retracted position within lumen 51 of inner catheter 43 (as shown in FIG. 5), to an extended position wherein cutting head 48 and a distal portion of drive tube 52 extend beyond distal endface 60 (see FIG. 6). Button 62 of handle 44 signals controller 45 to extend and rotate cutting head 48 to cut a channel in the myocardium. Myocardial tissue severed by cutting head 48 is aspirated through lumen 54 of drive tube 52 to tissue trap 53 to reduce the risk that the severed tissue will embolize. Cutting head 48 preferably is constructed of a radio-opaque material or includes band 65 of radio-opaque material, such as platinum-iridium, disposed on its proximal end to assist in visualizing the location of the cutting head under a fluoroscope.

Referring to FIG. 6, outer guide catheter 42 and inner catheter 43 preferably include preformed bends. In particular, by rotating outer guide catheter 42 (indicated by arrows A) or inner catheter 43 (as indicated by arrows B) relative to one another, or extending inner catheter 43 longitudinally with respect to outer guide catheter 42 (as indicated by arrows C), distal endface 60 of inner catheter 43 may be disposed at a plurality of tissue contacting locations. Accordingly, outer guide catheter may disposed at a first orientation relative to an endocardial surface, and then inner catheter 43 may be moved relative to outer catheter 42 to form channels at a plurality of positions along the path indicated by arrows B. Outer catheter 42 may then be moved along the path indicated by arrows A, and a new series of holes may then be formed at that position by further rotating inner catheter 43. As will of course be understood, needle stabilizer 59 and cutting head 48 are retracted when moving between one channel forming position and another.

Figure 7A:
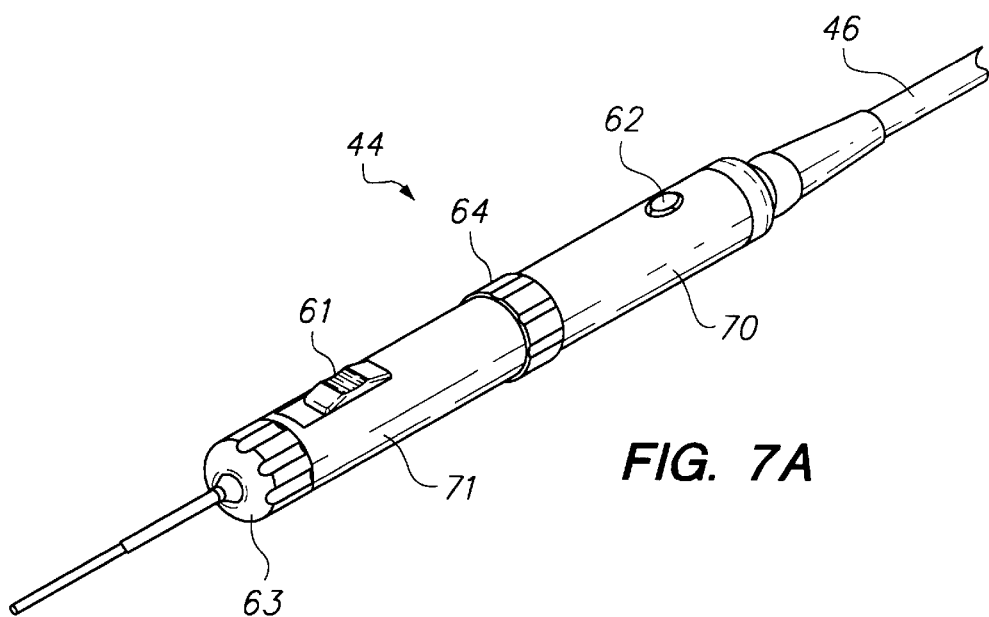
FIGS. 7A and 7B are, respectively, a perspective view and sectional view of an illustrative handle of the apparatus of FIG. 4.
Figure 7B:
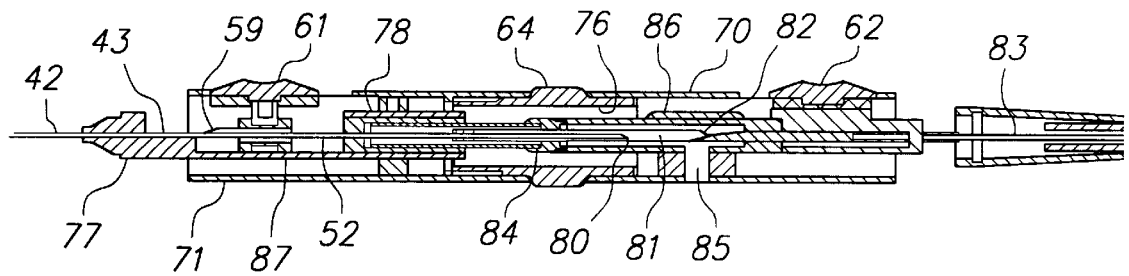

Referring now to FIGS. 7A and 7B, an illustrative arrangement of the components of handle 44 is described. Handle 44 comprises proximal and distal portions 70 and 71, respectively, joined so that distal portion 71 may be rotated independently of proximal portion 70. Proximal portion 70 is coupled to cable 46 and includes button 62 for activating the cutting head to bore a channel. Distal portion 71 is affixed to inner catheter 43 so that rotation of knob 63 of portion 71 is transmitted to the distal end of inner catheter 43.

Slider button 61 is coupled to needle stabilizer 59, so that movement of button 61 in the distal direction deploys needle stabilizer 59, and movement of button 61 in the proximal direction retracts needle stabilizer 59 within lumen 58 of inner catheter 43. Needle stabilizer 59 includes a lumen through which the autologous angiogenic agent is injected, as described hereinabove, for example, by depressing button 61. Wheel 64, if provided, is coupled to inner catheter 43 to permit optional adjustment of the cutting depth attained by cutting head 48.

With respect to FIG. 7B, wheel 64 is disposed within tubular member 76 and extends within portions 70 and 71. Inner catheter 43 is coupled to a rigid tubular member (e.g., stainless steel hypotube) that extends through element 77. Element 77 in turn is coupled through tubular member 78 to distal portion 71, so that rotation of distal portion 71 is transmitted to inner catheter 43. Tubular member 76 is coupled by threads to tubular member 78 so that rotation of wheel 64 causes inner catheter to be moved in a distal or proximal direction relative to drive tube 52 (depending upon direction of rotation), thereby lengthening or shortening the stroke of cutting head 48 beyond distal endface 60 of the inner catheter.

Drive tube 52 has proximal end 80 affixed to tubular member 81 having skive 82. Tubular member 81 is coupled to drive wire 83. Tubular member 81 is disposed for rotational and longitudinal motion, imparted by drive wire 83, within tubular member 84. The distal end of tubular member 84 is disposed within tubular member 78, while the proximal end includes a suitable bearing that seals against tubular member 81 without binding. Tissue passing through lumen 54 of drive tube 52 exits through skive 82 into the interior of tubular member 84, and then aspirated through port 85 into vacuum hose 47. Tubular member 84 is affixed to the interior of proximal portion 71 by element 86, which also supports button 62. Needle stabilizer 59 is fastened to slider button 61, which is in turn coupled to spool 77 to provide rigidity to the assembly. Needle stabilizer also includes a port that permits the lumen of the needle to be coupled to a vial or syringe containing autologous angiogenic agent.

Handle 44 therefore provides the ability to rotate distal portion 71 of the handle to orient the bend in inner catheter 43, while retaining button 62 on top of proximal portion 70 facing upward. Slider button 61 permits needle stabilizer 59 to be selectively deployed, and knob 63 permits the inner catheter to be rotated relative to the outer guide catheter. Wheel 64 permits the inner catheter to be translated distally or proximally with respect to the cutting head, to account for the effects of inserting the distal portion of device 41 along a tortuous path.

Figure 8:
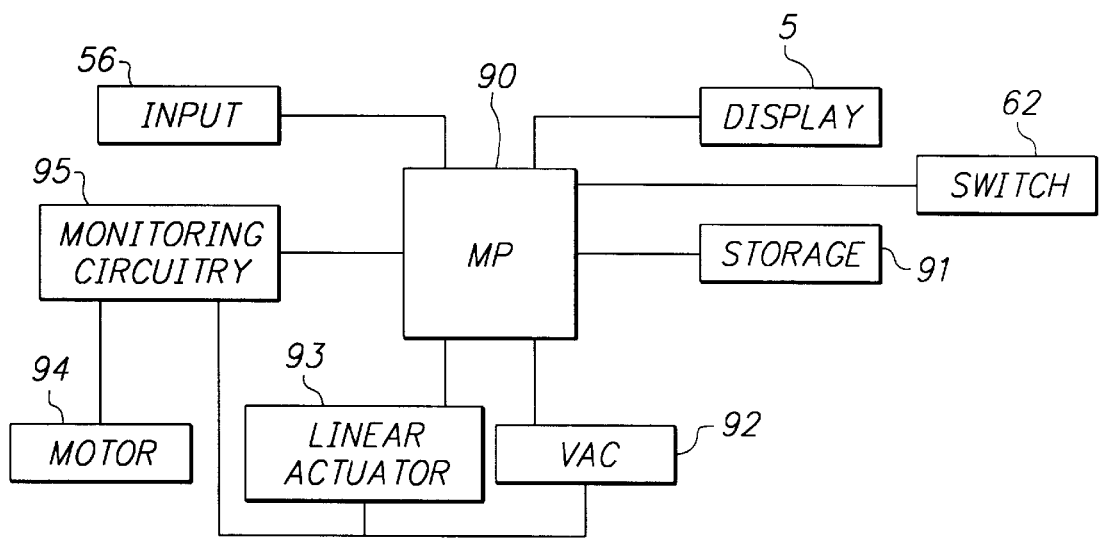
FIG. 8 is a block diagram of the components of a controller constructed in accordance with the present invention.

With respect to FIG. 8, a block diagram of the components of controller 45 are described. Controller 45 preferably comprises microprocessor 90 coupled to display panel 55, input device 56 (e.g., keyboard), activation button 62 of handle 44, data storage 91 (e.g., RAM and ROM or hard disk), vacuum pump 92, linear actuator mechanism 93 (e.g., a worm screw drive or pneumatic cylinder), motor 94 and monitoring circuitry 95. Monitoring circuitry 95 may be coupled to components 92–94, for example, to monitor the level of vacuum drawn by vacuum pump 92, or a motor parameter, such as the displacement of or linear force applied by linear actuator mechanism 93 and/or the speed of or electrical current drawn by motor 94.

For example, monitoring circuitry 95 may be arranged to ensure that the cutting head is not extended unless there is an appropriate level of suction being drawn through drive tube 52 and cutting head 48, or that the cutting head is rotating at a desired RPM before being advanced into tissue. Additional applications for monitoring circuitry 95 are described in the above-incorporated, commonly assigned U.S. Pat.

Figure 9A:
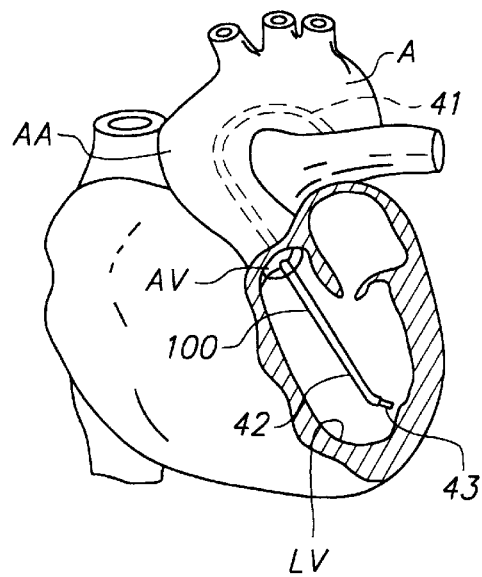
FIGS. 9A–9C are views illustrating deployment and use of the apparatus of FIG. 3 to percutaneously form channels in the myocardium and inject autologous angiogenic agents.
Figure 9B:
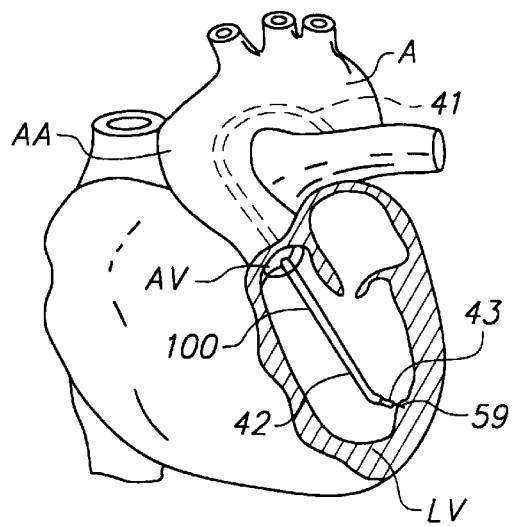
Figure 9C:
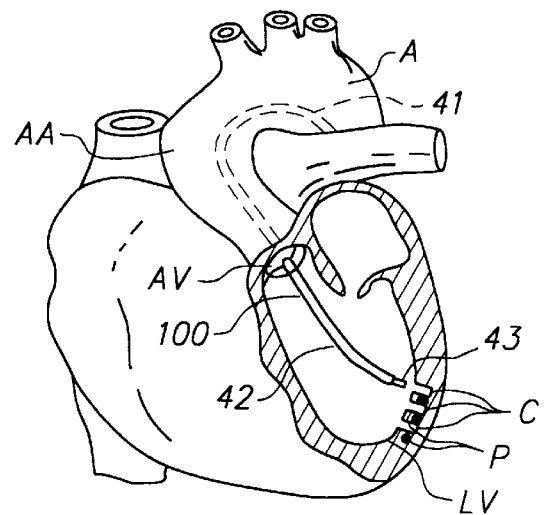

Referring now to FIGS. 9A–9C, a method of using the apparatus of the present invention perform PMR and to inject autologous angiogenic agents is described. In FIG. 9A, distal region 100 of device 41 of FIG. 1 is shown positioned in a patient's left ventricular cavity, using techniques which are per se known. Specifically, distal region 100 of device 41 is inserted via a femoral artery, and is maneuvered under fluoroscopic guidance in a retrograde manner up through the descending aorta, through aortic arch A, and down through ascending aorta AA and aortic valve AV into left ventricle LV. Previously known imaging techniques, such as ultrasound, MRI scan, CT scan, or fluoroscopy, may be used to verify the location of the distal region 100 within the heart.

In FIG. 9B, slider button 61 on handle 44 is advanced to extend needle stabilizer 59 so that it penetrates into the myocardium a predetermined distance, for example, 7 mm. Button 62 on handle 44 then is depressed, causing the drive system of controller 45 to extend cutting head 48 to bore a channel into the myocardium to a predetermined depth. Alternatively, button 62 of handle 44 may be omitted, and controller 45 instead programmed so that linear actuator 93 causes the cutting head to be extended a predetermined interval of time (e.g., 1 second) after slider button 61 is actuated. In this alternative embodiment, slider button 61 will of course have to generate a signal that is communicated to controller 45 via cable 46.

When cutting head 48 engages the endocardium, a reaction force is generated in inner catheter 41 that tends both to push distal region 100 away from the tissue. Needle stabilizer 59 counteracts these reaction forces and reduces transverse movement of the distal end of inner catheter 43, thus retaining the inner catheter in position while the cutting head is extended and retracted. Tissue severed by the cutting head is aspirated to trap 53 of controller 45.

Once cutting head reaches its maximum extension, as determined by any of the means described hereinabove, processor 90 causes forward motion of the cutting head to cease. In the embodiments using linear actuator 93, processor 90 also issues a command to reverse the direction of linear actuator 93. This in turn causes cutting head 48 to be withdrawn from channel C formed in the myocardium to a position just below distal endface 60 of inner catheter 43. Button 61 is then depressed to inject a bolus of autologous angiogenic agent into the myocardium at a location adjacent to channel C.

Advantageously, the needle stabilizer of device 41 permits an angiogenic agent to be injected at a location a predetermined distance from the channel formed by cutting head 48. By comparison, use of a separate needle catheter to inject an angiogenic agent into the myocardium after the channel forming process is completed would result in the angiogenic agent being injected at random locations relative to the previously formed channels.

As shown in FIG. 9C, a matrix of spaced-apart channels C and associated pockets of angiogenic agent may be formed in the wall of left ventricular wall LV by rotating outer guide catheter 42 and inner catheter 43 relative to one another (see FIG. 6). Needle stabilizer 59 and cutting head 48 are then advanced at each position to form further channels C in the tissue. The foregoing methods therefore enable a matrix of channels to be formed in the left ventricular wall. It is believed that such channels may be drilled anywhere on the walls of the heart chamber, including the septum, apex and left ventricular wall, and the above-described apparatus provides this capability.

While preferred illustrative embodiments of the invention are described, it will be apparent that various changes and modifications may be made therein without departing from the invention, and the appended claims are intended to cover all such changes and modifications that fall within the true spirit and scope of the invention.

What is claimed is:

1. A method of performing percutaneous myocardial revascularization of a patient comprising:
   collecting autologous biological material from the patient;
   preparing the autologous biological material to form an angiogenic agent;
   providing a catheter adapted for insertion into the left ventricle comprising a hollow stabilizer element and a cutting head movable from a retracted position to an extended position;
   advancing a distal region of the catheter transluminally to a position within the patient's left ventricle;
   deploying the stabilizer element to stabilize the distal region of the catheter in contact with an endocardial surface;
   advancing the cutting head from the retracted to the extended position to bore a channel into the patient's cardiac tissue; and
   injecting an amount of the angiogenic agent through the hollow stabilizer element into a region of the patient's cardiac tissue adjacent to the channel.

2. The method of claim 1 wherein the stabilizer element comprises a first retractable needle and deploying the stabilizer element comprises advancing the retractable needle to penetrate into the patient's cardiac tissue.

3. The method of claim 1 wherein collecting autologous biological material from the patient comprises collecting a quantity of whole blood from the patient.

4. The method of claim 3 wherein preparing the autologous biological material comprises centrifuging the whole blood to form a platelet-rich plasma.

5. The method of claim 4 wherein preparing the autologous material further comprises activating the platelet rich plasma.

6. The method of claim 5 wherein activating the platelet rich plasma further comprises activating the platelet rich plasma with purified thrombin.

7. The method of claim 1 wherein collecting autologous biological material from the patient comprises harvesting cells from the patient's cardiac tissue or bone marrow.

8. The method of claim 7 wherein preparing the autologous material further comprises culturing the harvested cells in vitro.

9. The method of claim 1 further comprising aspirating cardiac tissue severed by the cutting head.

10. The method of claim 1 further comprising, after the step of preparing an angiogenic agent, storing the angiogenic agent under refrigeration.

11. A method of performing percutaneous revascularization of a patient's cardiac tissue, the method comprising:
   collecting autologous biological material from the patient;
   preparing the autologous biological material to form an angiogenic agent;
   providing a catheter adapted for insertion into the left ventricle comprising a hollow needle movable from a retracted position to an extended position and a cutting head movable from a retracted position to an extended position;
   advancing a distal region of the catheter transluminally to a position within a patient's left ventricle;
   advancing the hollow needle to the extended position to penetrate and stabilize the distal region of the catheter in contact with an endocardial surface;
   rotating the cutting head;
   advancing the cutting head from the retracted to the extended position to bore a channel into the patient's cardiac tissue; and
   injecting an amount of the angiogenic agent through the hollow needle into a region of the patient's cardiac tissue adjacent to the channel.

12. The method of claim 11 wherein injecting an amount of the angiogenic agent comprises injecting a predetermined bolus of angiogenic agent to form a pocket of angiogenic material adjacent to the channel.

13. The method of claim 11 wherein collecting autologous biological material from the patient comprises collecting a quantity of whole blood from the patient.

14. The method of claim 13 wherein preparing the autologous biological material comprises centrifuging the whole blood to form a platelet-rich plasma.

15. The method of claim 14 wherein preparing the autologous material further comprises activating the platelet rich plasma.

16. The method of claim 15 wherein activating the platelet rich plasma further comprises activating the platelet rich plasma with purified thrombin.

17. The method of claim 11 wherein collecting autologous biological material from the patient comprises harvesting cells from the patient's cardiac tissue or bone marrow.

18. The method of claim 17 wherein preparing the autologous material further comprises culturing the harvested cells in vitro.

19. The method of claim 11 further comprising aspirating cardiac tissue severed by the cutting head.

20. The method of claim 1 further comprising, after the step of preparing an angiogenic agent, storing the angiogenic agent under refrigeration.

21. A method of performing percutaneous myocardial revascularization of a patient comprising:
   preparing biological material to form an angiogenic agent;
   providing a catheter adapted for insertion into the left ventricle comprising a hollow stabilizer element;
   advancing a distal region of the catheter transluminally to a position within the patient's left ventricle;
   deploying the stabilizer element to stabilize the distal region of the catheter in contact with an endocardial surface; and
   injecting an amount of the angiogenic agent through the hollow stabilizer element into the patient's cardiac tissue,
   wherein the stabilizer element comprises a first retractable needle and deploying the stabilizer element comprises advancing the retractable needle to penetrate into the patient's cardiac tissue.

22. The method of claim 21 further comprising, prior to preparing biological material, collecting the biological from the patient.

23. The method of claim 22, wherein the biological material comprises autologous biological material.

24. The method of claim 23 wherein collecting autologous biological material from the patient comprises collecting a quantity of whole blood from the patient.

25. The method of claim 24 wherein preparing the autologous biological material comprises centrifuging the whole blood to form a platelet-rich plasma.

26. The method of claim 25 wherein preparing the autologous material further comprises activating the platelet rich plasma.

27. The method of claim 26 wherein activating the platelet rich plasma further comprises activating the platelet rich plasma with purified thrombin.

28. The method of claim 23 wherein collecting autologous biological material from the patient comprises harvesting cells from the patient's cardiac tissue or bone marrow.

29. The method of claim 28 wherein preparing the autologous material further comprises culturing the harvested cells in vitro.

30. The method of claim 21, wherein the catheter further comprises a cutting head movable from a retracted position to an extended position.

31. The method of claim 30 further comprising, after deploying the stabilizer element, advancing the cutting head from the retracted to the extended position to bore a channel into the patient's cardiac tissue.

32. The method of claim 31, wherein injecting the angiogenic agent into the patient's cardiac tissue adjacent injecting into a region of the patient's cardiac tissue adjacent to the channel.

33. The method of claim 31 further comprising aspirating cardiac tissue severed by the cutting head.

34. The method of claim 21 further comprising, after the step of preparing an angiogenic agent, storing the angiogenic agent under refrigeration.

* * * * *